(12) United States Patent
Jussel (10) Patent No.: US 10,441,390 B2
(45) Date of Patent: Oct. 15, 2019

(54) DENTAL PRESS FURNACE

(71) Applicant: Ivoclar Vivadent AG, Schaan (LI)

(72) Inventor: Rudolf Jussel, Feldkirch-Gisingen (AT)

(73) Assignee: Ivoclar Vivadent AG, Schaan (LI)

(*) Notice: Subject to any disclaimer, the term of this patent is extended or adjusted under 35 U.S.C. 154(b) by 0 days.

(21) Appl. No.: 15/057,611

(22) Filed: Mar. 1, 2016

(65) Prior Publication Data

US 2016/0338805 A1 Nov. 24, 2016

(30) Foreign Application Priority Data

May 22, 2015 (EP) .................................... 15169054

(51) Int. Cl.
| | |
|---|---|
| *A61C 13/00* | (2006.01) |
| *A61C 13/20* | (2006.01) |
| *F27B 17/02* | (2006.01) |
| *A61C 13/083* | (2006.01) |
| *F27D 19/00* | (2006.01) |

(52) U.S. Cl.
CPC ...... *A61C 13/0021* (2013.01); *A61C 13/0022* (2013.01); *A61C 13/083* (2013.01); *A61C 13/20* (2013.01); *F27B 17/025* (2013.01); *F27D 19/00* (2013.01)

(58) Field of Classification Search
CPC . A61C 13/0022; A61C 1/0007; F27B 17/025; F27B 5/10; B30B 15/16
See application file for complete search history.

(56) References Cited

U.S. PATENT DOCUMENTS

| | | | | |
|---|---|---|---|---|
| 4,244,738 | A * | 1/1981 | Storchheim | ............... B22F 3/14 |
| | | | | 419/23 |
| 6,258,168 | B1 | 7/2001 | Pawelko et al. | |
| 6,303,059 | B1 | 10/2001 | Foser et al. | |
| 8,742,298 | B2 * | 6/2014 | Jussel | ................... F27B 17/025 |
| | | | | 219/390 |
| 8,890,036 | B2 * | 11/2014 | Serrago | ................. F27B 17/025 |
| | | | | 219/390 |
| 9,022,763 | B2 * | 5/2015 | Miller | ..................... A61C 13/20 |
| | | | | 264/16 |
| 2008/0099939 | A1 | 5/2008 | Jussel et al. | |

(Continued)

FOREIGN PATENT DOCUMENTS

| | | |
|---|---|---|
| CA | 2034893 A1 | 7/1991 |
| CN | 203908307 | 10/2014 |

(Continued)

*Primary Examiner* — Gregory A Wilson
(74) *Attorney, Agent, or Firm* — Ann M. Knab; Thad McMurray (57) ABSTRACT

The invention shows a dental press furnace comprising a pressing punch (36) which acts on a green product (32) made of in particular a ceramic mass—possibly by means of an interposed ram (28)—, the green product (32) being guided in a press channel (30) which is configured in a muffle (24), and a pressure, distance and/or speed sensor detecting at least one motion parameter of the pressing punch (36), and comprising a control device for controlling the pressing process based on the output signal of the sensor, the trigger criterion for the start of the pressing process being a change of at least one motion parameter of the pressing punch upon heating and/or softening of the green product which change is detected by means of the sensor.

17 Claims, 5 Drawing Sheets

(56) References Cited

U.S. PATENT DOCUMENTS

2009/0246739 A1* 10/2009 Jussel .................. A61C 13/20
433/223
2016/0184062 A1   6/2016 Jussel
2016/0338805 A1  11/2016 Jussel

FOREIGN PATENT DOCUMENTS

| EP | 0438802 A1 | 7/1991 |
|---|---|---|
| JP | 62231655 A | 10/1987 |
| JP | 201322460 A | 2/2013 |

* cited by examiner

DENTAL PRESS FURNACE

CROSS-REFERENCE TO RELATED APPLICATIONS

This application claims priority to European patent application No. 15169054.2 filed on May 22, 2015, the disclosure of which is incorporated herein by reference in its entirety.

TECHNICAL FIELD

The invention relates to a dental press furnace according to the preamble of claim 1, and to a method for operating a dental press furnace according to the preamble of claim 14.

BACKGROUND OF THE INVENTION

For a successful pressing process of a dental ceramic it is important to perform the heating process based on an exactly defined heating profile. Such a profile with a first comparatively high initial heating rate which is followed by a lower second heating rate is apparent from for instance, DE 10 2008 012 578 B4 and corresponding U.S. Pat. No. 9,033,703, which is hereby incorporated by reference.

In principle, such a heating curve is favorable for a satisfactory press result because in this connection, before the pressing is started, that is to say at an uncritical point in time, strong heating is carried out, and during the pressing process itself the material is pressed carefully.

EP 1 915 972 B2 and corresponding U.S. Pat. No. 8,317,512, which is hereby incorporated by reference, discloses a further improvement in this regard according to which an integral is used across a temperature/time area for detecting the amount of heat introduced.

While the temperatures measured typically relate to the internal temperature of the furnace and in this respect not to the real temperature of a green product, the document WO 2014/131588 A1 discloses a method for detecting the temperature of the green product itself.

With relatively long green products, however, there is a certain temperature gradient within the green product, and using the above-mentioned new and basically favorable solution which is, however, not completely uncomplicated, the temperature of the green product can typically be measured at one position but not at every position.

A further problem is that with particularly configured temperature profiles the dead time of the system of muffle/green product delays the measured temperature profiles. It is strongly dependent on the mass of the green product and of the muffle. This means that particularly voluminous muffles and large dental restoration parts, such as fourteen-unit bridges, should be operated in accordance with even "sharper", that is to say longer and more exact heating profiles.

In this respect, in order to comply with the necessary safety distance a holding time is typically inserted after the heating process which is to serve the temperature equalization and in which the hot external areas of the muffle give off their heat to the center of the muffle and thus to the green product.

However, this holding time prolongs the pressing cycle considerably depending on the size of the muffle, and in some cases this is not considered acceptable. Furthermore, depending on the muffle size used a corresponding control program comprising suitable temperature profiles and holding times must be selected. With today's large number of materials and programs for different muffles, the dental technician may make a wrong selection from time to time in the heat of the moment.

SUMMARY OF THE INVENTION

Thus, the invention is based on the task of providing a dental press furnace according to the preamble of claim 1 and a method for operating a dental press furnace according to the preamble of claim 14, which enables a shortened pressing cycle depending on the size of the dental restoration or else of the associated muffle.

This task is inventively solved by claims 1 and 14, respectively. Advantageous developments may be taken from the subclaims.

According to the invention it is particularly favorable that the inherent physical parameters of a green product, also known as an ingot or a blank, can be used as a criterion for the first time based on the invention. This represents significant progress even compared to solutions such as the solution disclosed in the above-mentioned DE 10 2008 015 483 B4 and corresponding US 2009246739, which is hereby incorporated by reference, and all the more compared to the typical and in some cases up to now extremely widespread firing furnaces and press furnaces in which only one temperature sensor is used in the interior of the furnace. In the solution according to WO 2014/131588 A1, which is improved compared to the above-mentioned solution, at least the surface of the dental restoration part to be produced is examined. However, in particular with relatively large green products there is a temperature gradient, and the size of the green product is also responsible for the temperature difference between the inside and the outside. A further disadvantage of the aforesaid solution is the need to attach additional and expensive measurement technology to the device.

Typically, a temperature gradient exists in a muffle whose isotherms extend substantially bell-shaped in a three-dimensional view, wherein—in terms of the green product—at the bottom center of the green product the temperature is lowest and at the top/on the outside of the green product the temperature is highest. Inventively, green product parameters on the side faces of the green product are used as trigger criterion in a surprisingly subtle manner and the entire green product and its temperature are evaluated.

According to the invention, trigger conditions from previous processing steps which are not ideal, such as a correct preheating temperature or preheating duration of the muffle, are also taken into account or corrected or balanced, respectively.

The green product will be pressurized—long before the actual pressing process takes place—by the pressing punch—typically by means of an interposed ram, for instance made of $Al_2O_3$. A force and pressure act on its upper front surface and are absorbed by its bottom side, and in some cases lead to an elastic deformation of the green product—if only to a very small extent. In any case, this force and the deformation are sufficient to bridge the clearance which is reserved for inserting the green product into the press channel of the muffle.

Typically, the muffle mass has a comparatively low coefficient of thermal expansion of for instance $3 \times 10^{-6}/°K$, while the green product made of ceramics has a considerably higher coefficient of thermal expansion of for instance $10^{-5}/°K$.

Green products made of ceramics comprise a coefficient of thermal expansion of for instance 10 or $10.5 \times 10^{-6}/°K$ until below the region that is referred to as glass transition region. In fact, the coefficient of thermal expansion rises considerably when the so-called second-order phase transition is exceeded, for instance to $14.5 \times 10^{-6}/°$ K. However, due to the softening of the green product particularly the shape of the green product is also changed; as far as it is not in contact with the wall of the press channel, contact is made now. In particular, the green product also starts to enter into the sprue channels for the cavities of the dental restorations as it has become viscous by now. This presents a considerable overcompensation of the increasing coefficient of thermal expansion.

In an advantageous embodiment it is provided that the micro impulses have a motion time and motion distance which is smaller than the total motion distance of the green product and the total residual time by more than one order of magnitude, in particular by more than two orders of magnitude, the length of the micro impulses amounting to particularly between one millisecond and 500 milliseconds.

The micro impulses reflect a small and short-term motion between the upper end of the green product or the end which is close to the punch and the surrounding muffle. It is particularly favorable that in this way the temporal course of the thermal expansion as a consequence of the heating of the introduced system consisting of muffle, interposed ram and in particular the green product can be detected.

In a further advantageous embodiment it is provided that the control device determines the start of the pressing process independently of the temperature measured by the temperature sensor depending on the termination of the micro impulses.

In a further advantageous embodiment it is provided that the control device starts the start of the pressing process based on an increase in the measured time period between two consecutive micro impulses above a predefined threshold value.

In a further advantageous embodiment it is provided that the control device reduces the heating power to a nominal value when the time period between two consecutive micro impulses rises above a predefined, in particular second threshold value.

According to the invention, the time profile of the micro impulses is evaluated and a trigger criterion for the start of the pressing process is determined either upon termination of the micro impulses of the motion parameters of the green product and/or upon detection of a predefined number of micro impulses and/or by evaluating the temporal distance between the micro impulses.

Thus, the invention can be used to determine and define the ideal start of the pressing process and can thus lead the total time spent on the pressing cycle close to the optimum.

In accordance with the invention, as viewed from the motion parameters, as a trigger criterion for the actual pressing process the occurrence of short-term micro movements is monitored and used as a criterion. It is to be understood that the micro movements are directed against the direction of pressing due to the thermal expansion of the total system of pressing punch/ram/green product/muffle/sheath of the firing chamber.

The pressing punch is moved to a predefined extent against the direction of pressing while the green product is heated, which extent amounts to in particular less than 1 mm and particularly preferable to between 0.3 and 0.5 mm, measured at typical heights of the green products of 8 to 16 mm.

A distance sensor or a speed sensor is primarily suitable for detecting the micro motion which is basically represented as a micro impulse of a motion parameter. The resolution should amount to at least 0.01 mm or a respective speed value, preferably 50 mm per second.

Otherwise, for instance if the press force is exerted by means of a stepping motor comprising a non-elastic or slightly elastic drive train, it is also possible to realize a power sensor or pressure sensor as a sensor for detecting the micro impulses. Alternatively, it is also possible to have a mere distance measurement, possibly at a press force of close to zero.

As a matter of course, the amplitude and frequency of the micro impulses depend on physical parameters such as the ceramic material to be pressed, the used investment material, the temperature, but also, for instance, the press force exerted or its regulation.

The thermal expansion counteracting the press force is substantially composed of the thermal expansion of the pressing punch, the ram, the green product and the muffle below the green product. The insulation region of the furnace below the firing chamber bottom is also heated slightly and expands correspondingly.

The fact that the pressing punch is in contact with the interposed ram and thus with the green product, preferably under contact pressure, can be used particularly favorably. The press force can be transmitted without a delay in time, as is the case with the backward motion when the material of the green product expands. The control device for controlling the pressing process does not only detect said expansion but also controls the further course of the temperature-time profile.

Due to the good thermal insulation the furnace is practically cold, typically between room temperature and 50° C., typically on the outside and thus at the supporting positions which are responsible for closing the furnace—at least when considered in relation to the hot firing chamber—, such that the heating existing thereat that basically contributes to the detectable thermal expansion of the above-mentioned elements is relatively low.

In this connection, it is assumed that the heating surrounds the cylindrical firing chamber laterally in a way known per se as a ring heating and heats primarily the muffle but of course also the green product located therein and possibly the ram by means of convection and thermal radiation, typically in a few minutes by several 100° C. In typical press furnaces, the wall thickness of the thermal insulation amounts to ten centimeters or more and is thus within the range of the diameter of the muffle or larger.

The heating in the drive train comprised of ram, pressing punch, green product and investment material in the lower part as well as possibly the firing tray and the surrounding parts produces counterpressure acting onto the press drive.

If no further motion impulses are produced, the heating of the green product is advanced to such an extent that the green product has become at least doughy.

Basically, pressing the green product by introducing a press force would already be possible at this point in time. However, it is more favorable to wait until a predetermined, defined time period has elapsed and to then start the pressing process in order to exploit the fact that the viscosity of the green product is continuously decreased when more heat is supplied and that the ideal viscosity for starting the pressing process is reached when a certain amount of heat has been supplied over a predefined period of time.

According to the invention it is possible to use the same press force during the inventive detection of the trigger criterion as during the actual pressing process.

However, it is preferable to select an auxiliary press force of between thirty and fifty percent of the nominal press force as this is already sufficient to produce the desired motion hysteresis.

It is also possible to keep the press force at a comparatively high value for a short period of time immediately after feeding the pressing punch towards the ram—and thus indirectly towards the green product—in order to ensure stable contact of the green product in the muffle and to then readjust the press force.

The point in time of the ideal start of the pressing process as from the softening of the green product largely depends on how fast the green product continues to be heated from this point in time. As larger muffles have a larger heat capacity and thus also a better thermal insulation, the defined time can be set considerably longer with larger muffles from the outset, and correspondingly shorter with smaller muffles.

In a further advantageous embodiment it is possible to evaluate the micro impulses, their course and their succession and to store them in a control device for the dental press furnace. Depending on the material, the succession and the type of micro impulses is different such that a green product of a particular size and made of a particular material automatically comprises a signature based on the micro impulses thereof. Said signature can be used for selecting further suitable process parameters in an advantageous embodiment.

On the basis of the time period until the green product softens a respective ideal waiting time and temperature-time control until the start of the pressing process can be determined. A further advantage particularly with regard to the ease of use is that the selection of separate programs depending on the size of the muffle used is omitted.

A further aspect which is relevant for the accuracy of the measurements which have been taken is providing the negative pressure in the furnace before the measurement is taken. By means of the negative pressure in the furnace the seals between the furnace hood and the furnace bottom, or for instance between the furnace hood and an approachable firing tray, are compressed to the predefined extent. Indeed, the compression can be in a range of several millimeters and would falsify the measurement result if the negative pressure was built during the pre-pressing time, that is to say during the detection of the trigger criterion.

If—for whatever reasons—the negative pressure, as is desired during the pressing cycle, is not to be provided completely during this time, it has to be ensured that the negative pressure in the interior of the furnace remains constant during this pre-pressing time.

Provided that the furnace is sufficiently sealed, the negative pressure can be provided typically within a considerably shorter time than required for heating the furnace, for instance within 1 to 2 minutes.

According to a preferred embodiment, a force control is provided for the press drive. Due to the heating process and thus the thermal expansion of the drive train (including the green product) readjustment has to be carried out, for instance upon exceeding a predefined force. If this readjustment characteristic is adjusted correspondingly well a number of micro impulses can be realized which is easy to be interpreted qualitatively and quantitatively. During the heating of the green product in a still solid physical state the distance between the micro impulses and/or the distance between the intervals in which the force is readjusted increases exponentially.

As a trigger criterion the end of the micro impulse series can for instance be used, approximated by the absence of an impulse for instance for more than 50 seconds.

However, it is possible to count the number of impulses without further ado and to determine the trigger criterion based upon this. Furthermore, it is also possible to use the amount of the time difference between two successive impulses as a trigger criterion.

BRIEF DESCRIPTION OF THE DRAWINGS

Further advantages, details and features may be taken from the following description of an exemplary embodiment of the invention in conjunction with the drawings in which.

DETAILED DESCRIPTION

Figure 1:
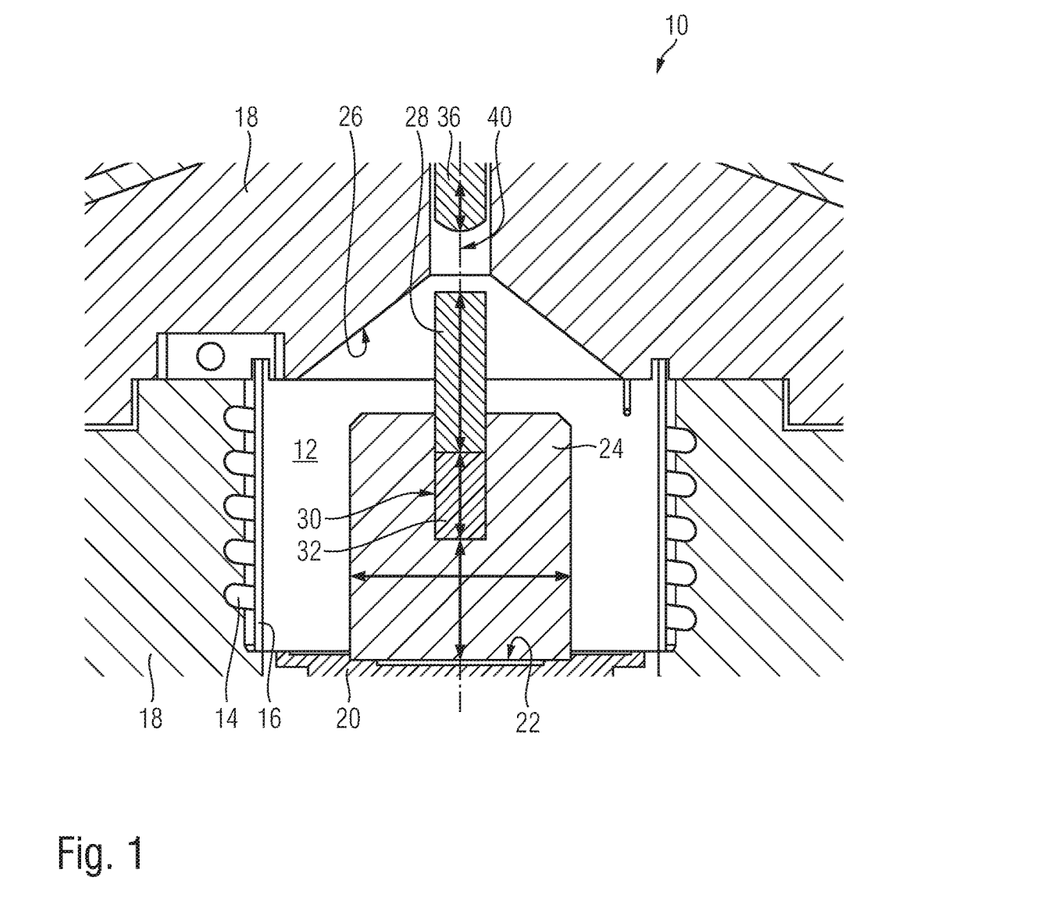
FIG. 1 shows a section through the firing chamber of an inventive dental press furnace in one embodiment.

FIG. 1 illustrates a section through an inventive dental press furnace 10 showing a portion which is relevant for the invention.

A firing chamber 12 is surrounded by a heating device 14 which is illustrated schematically and comprises a helically extending heating coil which is shielded by a quartz glass 16 as a protective device. Large-volume thermal insulation elements 18 surround the firing chamber 12 on all sides, that is to say also towards the bottom, even if this is not obvious from FIG. 1.

The bottom of the firing chamber 12 is formed by a firing tray 20 which comprises recesses 22 for receiving the muffle 24, in fact graduated by different sizes, two sizes in the exemplary embodiment illustrated.

Muffles of different sizes are required if dental restoration parts of different sizes whose female molds are realized in the muffle are to be pressed and fired. Thus, for instance a fourteen-unit bridge requires a larger muffle than three individual crowns which can be fired correspondingly using a smaller muffle such as a muffle with a muffle mass of 100 g. In this connection, muffle sizes of 100, 200 and 300 g are typical.

The firing chamber 12 comprises a roof cone 26 which expands the firing chamber centrally towards the top. In this area, a part of a ram 28 is received which is inserted into a press channel 30, in contact with a green product 32 which is received in the muffle 24 in the press channel 30 completely.

Sprue channels and mold areas (not illustrated) for dental restoration parts extend below the green product. In a way known per se, the diameter of the sprue channels is substantially smaller than the diameter of the press channel 30 such that the green product 32 can only start to enter into the sprue channels once it softens.

The ram can consist of any suitable material, for instance of $Al_2O_3$ or from an investment material itself.

In a pressing punch channel a pressing punch 36 is guided which is driven by a drive unit and which can exert pressure onto the ram 28 and thus indirectly onto the green product 32.

In order to operate the dental press furnace, the furnace is initially opened. A muffle which has been pre-heated to 850° C. in a furnace referred to as a pre-heating furnace and into which a cold green product 32 and a cold ram 28 have already been inserted is positioned centrally on the firing tray 20. The dimensions of the recess 22 exactly match the associated muffle 24 such that the muffle 24 is positioned exactly in the center. The furnace hood is closed and a negative pressure source draws air present in the firing chamber 12 and in the thermal insulation elements until negative pressure is produced.

Seals are provided between a furnace base unit and the firing hood of the furnace which are compressed as the negative pressure becomes stronger. The negative pressure is built up within one to two minutes and is kept constant during the entire following press cycle, for instance by regulating the pressure of the negative pressure source or by continuing to run the corresponding suction pump.

As soon as the green product 32 has been inserted into the muffle 24 the heating of the green product 32 starts which has a considerably smaller mass than the muffle 24. Because of this, the green product expands wherein the pre-heating temperature is considerably below the softening temperature. The green product is guided in the press channel 30 with small clearance. The coefficient of thermal expansion of the muffle 24, that is to say of the investment material which is used for forming the muffle, is considerably smaller than the coefficient of thermal expansion of the green product and of the ram and the pressing punch, wherein the pressing punch can for instance also consist of $Al_2O_3$ or for instance of steel.

In the exemplary embodiment illustrated herein, the coefficient of thermal expansion of the muffle is $3 \times 10^{-6}/°K$ and of the green product is $10 \times 10^{-6}/°K$, and that of the pressing punch is $8 \times 10^{-6}/°K$.

In the thermal expansion in axial direction considered herein the thermal expansions $L_0$ sum up during the heating. The total thermal expansion $L_{0\ tot}$ is:

$$L_{0\ tot} = L_{0\ IVM} + L_{0\ green\ product} + L_{0\ Alox\ ram} + L_{0\ pressing\ punch}$$

In this connection, the pressing punch 30 only needs to be taken into account in as much as it is heated, that is to say in the region of the thermal insulation elements 18 adjacent to the firing chamber.

The opposite end of the pressing punch 36 which is connected to the drive unit is considerably less hot, for instance under 100° C.

The temperature gradient of the pressing punch 36 is high in particular if a pressing punch for instance made of $Al_2O_3$ is used; if a metallic pressing punch is used, an additional thermal insulation cylinder may be integrated into the pressing punch.

$L_{0\ IVM}$ is the axial length of the muffle or investment material below the press channel 30.

In the illustrated embodiment of a dental press furnace the firing tray 20 is only warm on its surface and comparatively cool in the lower region. However, this does not hold true if a heating referred to as a base heating of a firing chamber is realized, that is to say if a further heating is provided below the firing tray 20. In this embodiment the additional thermal expansion in the region thereat needs to be added to the above-mentioned total thermal expansion.

In order to identify the axial displacement of the pressing punch 36 as a consequence of the thermal expansion the thermal expansion of the press furnace itself upon heating needs to be deducted from $L_{0\ tot}$. However, in this connection it must be taken into account that the sealing and the closing force of the furnace are typically realized far to the outside and that the thermal expansion thereat is typically limited to a range between room temperature and a temperature below 100° C., for instance 60° C.; the thermal insulation elements 18 that become very hot at least on the inside do not exert any axial forces but are supported easily in the dental press furnace.

Here, axial refers to the axis 40 of the pressing punch 36 which runs centrally through both the ram and the green product 32 as well as through the muffle 24 and the firing tray 20; all elements are configured circular symmetrically in the exemplary embodiment illustrated.

Figure 2:
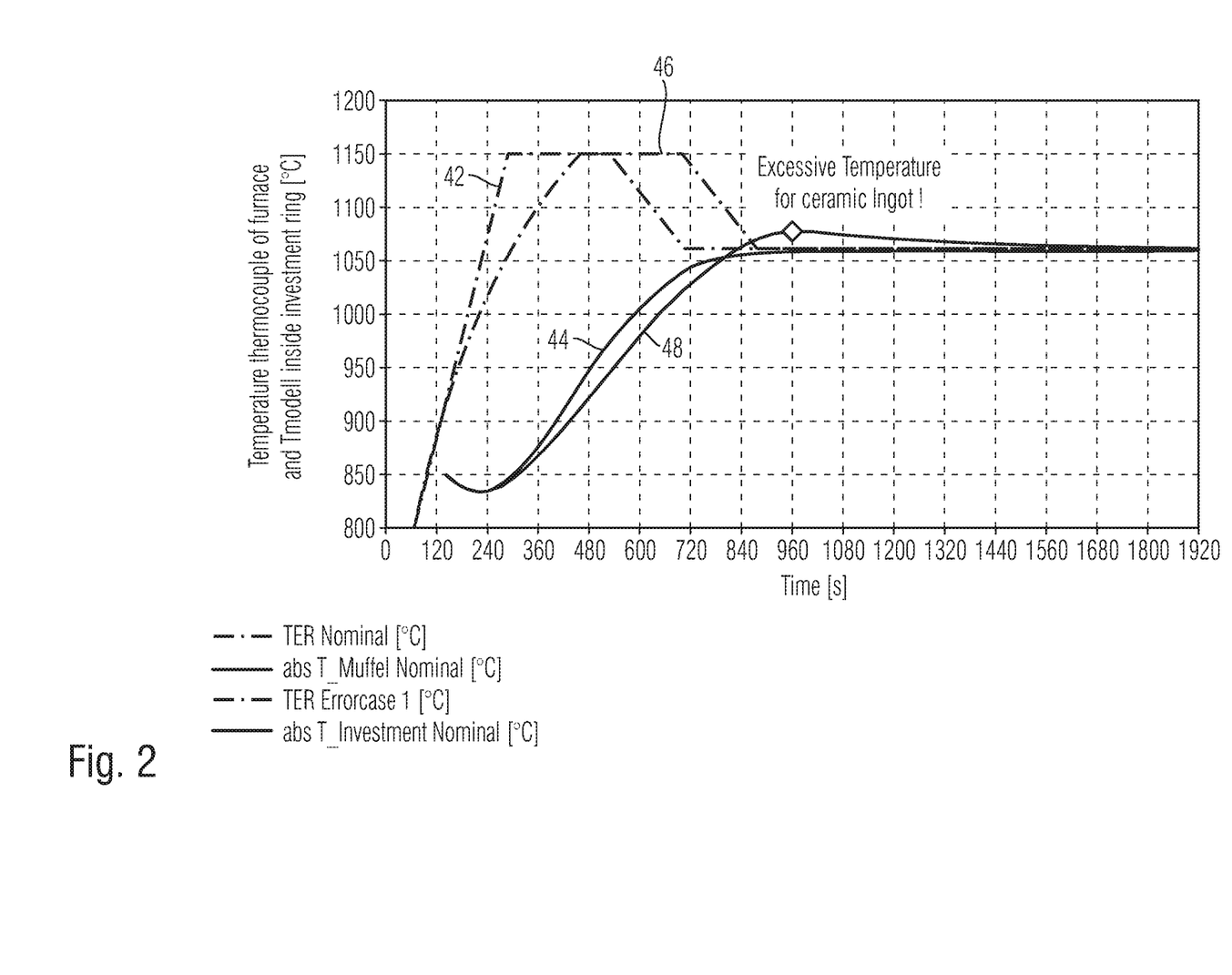
FIG. 2 shows a diagram illustrating a possible heating curve, also compared to an inadmissible heating curve.

FIG. 2 discloses a typical firing/press curve in two embodiments. In the temperature curve 42 the requirement of the so-called temperature-time area monitoring according to EP 1 915 972 B1 is met. This leads to the muffle temperature curve 44. As can be seen, the muffle temperature curve does not exceed 1065° C. if the program is operated accurately according to the heating temperature curve 42 such that the green product cannot be damaged.

However, the heating temperature curve 46 does not take into account the requirements of the temperature-time area monitoring according to EP 1 915 972 B1—although the maximum temperature of 1150° C. is not exceeded and the time period of the maximum temperature is not greater than with the heating temperature curve 42.

Still, this heating temperature curve leads to the muffle temperature curve 48 and it is obvious that a muffle temperature of 1075° C. is reached at the point in time of 960 seconds which can lead to damage to the green product. The inventive dental press furnace is controlled by a control device (not shown).

The inventive solution can be combined particularly easily with the proper requirements according to EP 1 915 972 B1 but is basically independent thereof. Now, the inventive solution is explained based on the diagram of FIG. 3.

Figure 3:
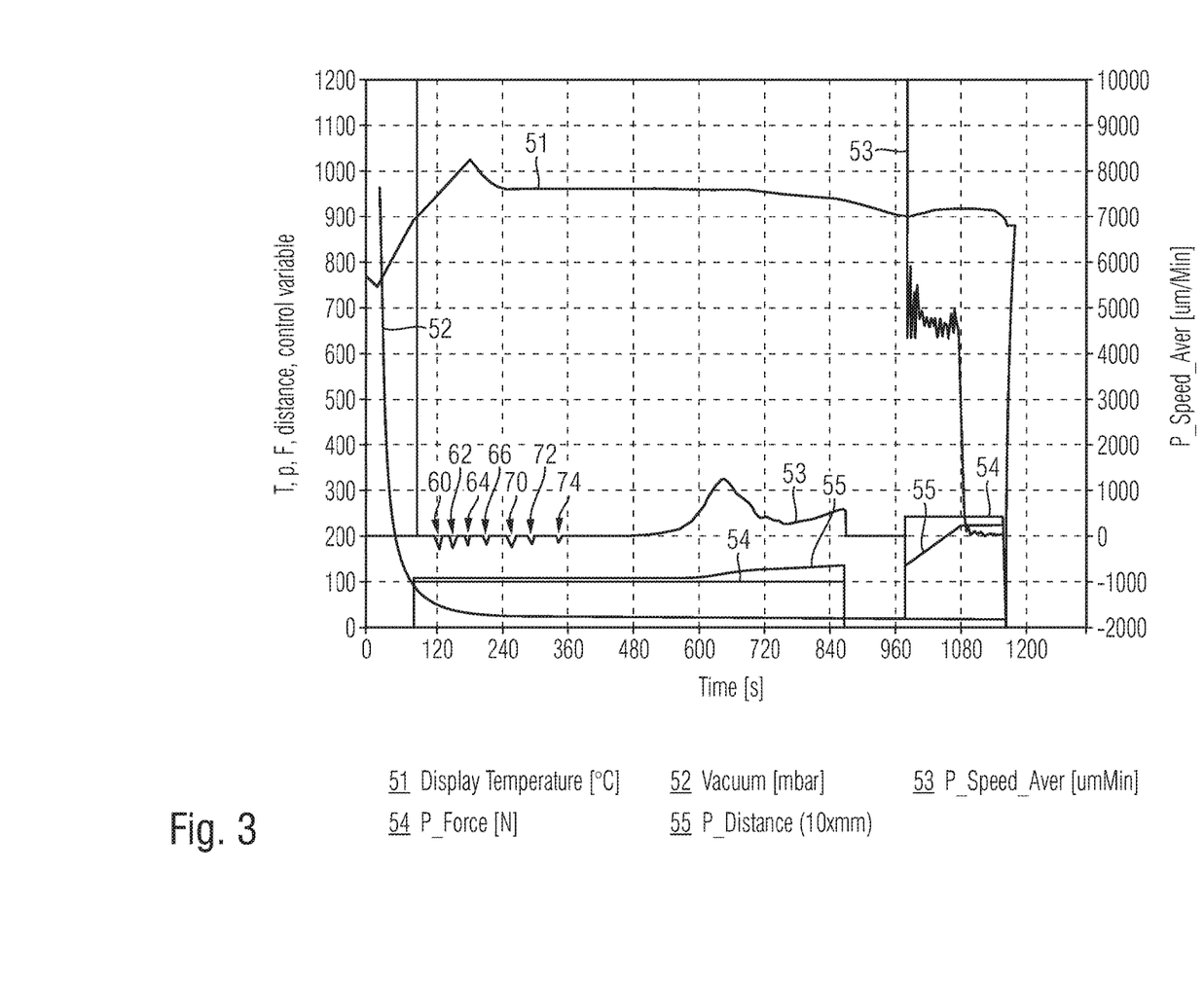
FIG. 3 shows a diagram illustrating the speed of the pressing punch and further physical quantities, plotted over time.

In FIG. 3 five curves are plotted in the same diagram and the axis of abscissas is time.

Here, the following values are concerned:

The temperature curve 51 shows the temperature displayed in the display of the firing furnace, measured by means of a temperature sensor known per se in the firing chamber.

The pressure curve 52 shows the pressure in the interior of the dental press furnace.

The speed curve 53 shows the speed of the pressing punch 36 or of the associated drive unit.

Here, the neutral point of the ordinate is vertically offset and the speed values in mm/min are recorded on the right hand side.

The applied press force is recorded in the press force curve 54.

The distance covered by the pressing punch 36 is recorded in the distance curve 55.

As can be seen from FIG. 3 the dental press furnace 10 has already been pre-heated to approximately 750° C. at the considered beginning. The heating continues working and heating is carried out according to the temperature-time area monitoring (see FIG. 2), wherein the target temperature is between 900° C. and 1000° C. in the exemplary embodiment illustrated.

As can be seen from the pressure curve 52, the pressure in the dental press furnace drops rapidly within the first 20 seconds and amounts to 50 mbar at 120 seconds. At 240 seconds at the latest, the final pressure of 25 mbar is reached. This pressure is kept constant during the entire press cycle.

It is apparent from the speed curve 53 that at approximately 90 seconds, at the peak of the speed thereat, the pressing punch is brought close rapidly until pressing punch, ram and green product are in contact with one another. Here, the green product is supported by the front face of the press channel 30 in the muffle 24.

From 90 seconds to approximately 120 seconds the speed amounts to 0, as can be seen from FIG. 3.

At slightly more than 120 seconds an inventive micro impulse 60 at a negative speed is produced. This micro impulse 60 corresponds to a thermal expansion $DL_{0\ tot}$, as has been explained with regard to FIG. 1. The micro impulse has a height of approximately 200 mm/min and a duration of less than one second, depending on the quality of the press force regulation—even if this is not clearly evident from FIG. 3, either, based on the embodiment illustrated herein.

The upper end of the green product 32 automatically slides upwards slightly, contrary to the force of the press power according to the press curve 54.

Until the point in time of 145 seconds the speed 54 remains 0 constantly again, and at this point in time the next micro impulse 64 is produced at approximately 180 seconds and the next micro impulse 66 at 225 seconds. Further micro impulses 70, 72 and 74 follow at 250, 290 and 340 seconds, while the following period of time from 480 seconds remains free of micro impulses.

According to the invention, this means that the green product 32 has become doughy or viscous; in this connection, the further thermal expansion occurs without impulses. According to the invention, this fact is judged as an indication that the green product has reached the actual desired temperature for preparing of the actual pressing process.

Until the point in time of 860 seconds the green product 32 continues to soften and already penetrates partially into the sprue channels.

Subsequently, a security rest period of 120 seconds in this exemplary case is complied with, which is followed by the actual pressing process at increased press force.

As can be seen, then the green product penetrates into the dental restoration spaces rapidly, until at the point in time of 1040 seconds the speed of advance drops to almost 0 again according to the speed curve 53. This means that all cavities for providing the dental restoration are filled.

As can also be seen from FIG. 3, the press force amounts to 100N at the beginning of the delivery of the pressing punch 36. It remains constant until the point in time of 860 seconds and is then returned to zero. Between 980 seconds and 1130 seconds the press force amounts to 250N. Between 1130 and 1140 seconds it is returned to zero continuously.

It can be seen from the distance curve 55 that during the micro impulses 60 to 74 micro motions in the negative direction, that is to say in the direction opposite to the motion direction of the press drive, appear. Even if this is not explained separately, here the value 100 corresponds to the zero line of the motions. From approximately 480 seconds an initially small and then increasing motion with a correspondingly covered distance is produced until the motion stops at 860 seconds and is started again at 980 seconds. Naturally, the motion corresponds to the integral of speed, in correspondence with the increasing rise until approximately 1080 seconds, wherein in turn the motion is completed at 1140 seconds.

As can be seen from FIG. 3, the actual pressing process is not started immediately after the last micro impulse 74. Two different holding times are realized wherein it is to be understood that according to the invention it is also possible to work with only one holding time or without a holding time and for instance with an increasing press power from this point in time—that is to say without press break and with a constant press force, as illustrated herein.

For detecting the micro impulses it is basically possible to carry out a speed detection, a distance detection or a press force detection, depending on the resolution of the available sensors and depending on the elasticity of the drive. In tests in connection with the exemplary embodiment discussed herein, a press force detection has proven to be the most advantageous detection, whereas a distance detection is basically also possible.

Figure 4:
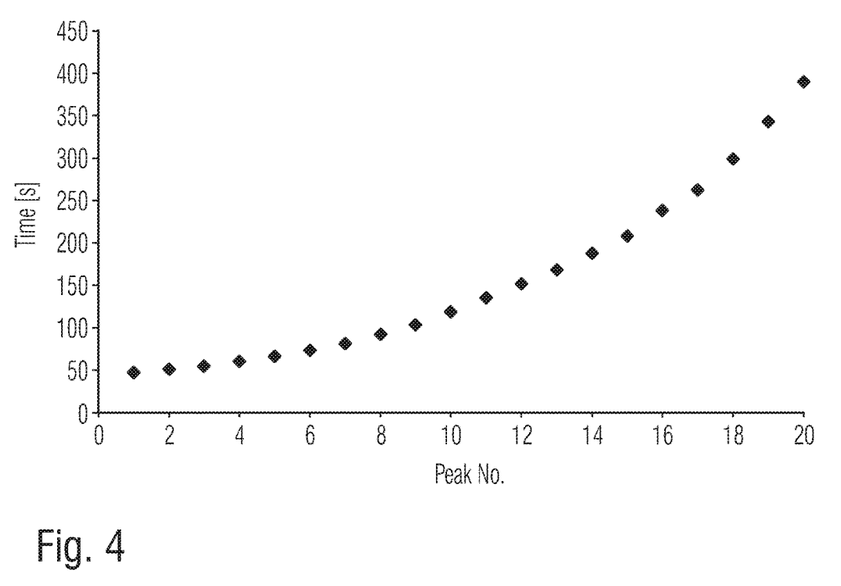
FIG. 4 shows a diagram illustrating the increasing distance between the micro impulses.

From FIG. 4 it can be seen how the micro impulses appeared in a further pressing test. Here, the elapsed time is plotted over the concerned micro impulse or peak. It is apparent that the curve comprises a substantially exponential course, that is to say that the period of time between the individual impulses increases exponentially. For instance, the time difference between the first and the second micro impulse amounts to only five seconds, however, to sixty seconds between the 19th and the 20th impulse.

Exceeding a period of time between two peaks can also be used as a trigger criterion for the actual start of the pressing process.

Figure 5:
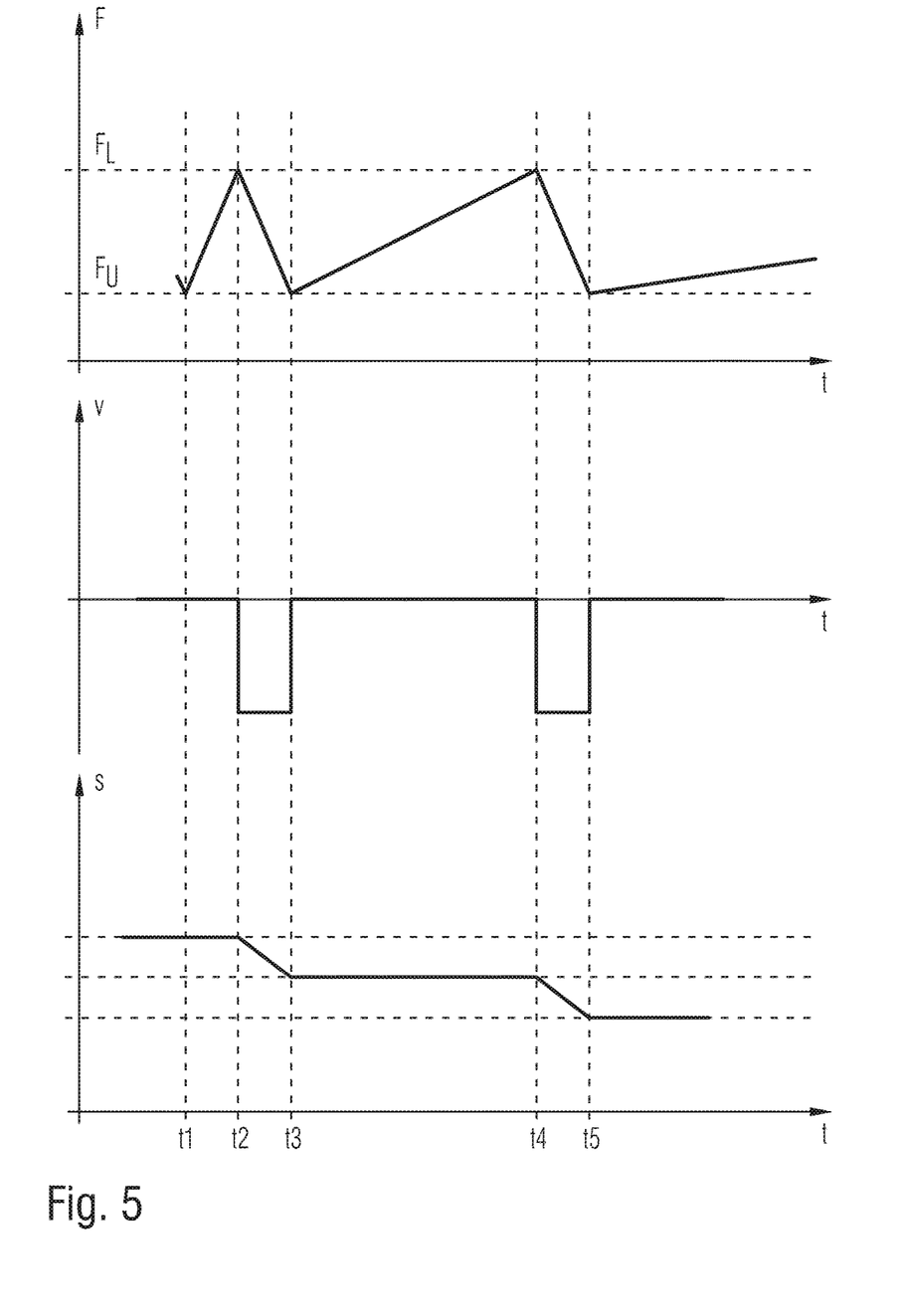
FIG. 5 shows three diagrams illustrating the progression of force, speed and distance during one micro impulse.

FIG. 5 shows schematically how a micro impulse, for instance the micro impulse 60, is represented with regard to speed, distance and force.

The uppermost curve shows the force F which increases until it reaches a limit $F_L$ upon contact with the green product due to the thermal expansion. The material relaxes by readjusting the press force from the point in time $t_2$ to the point in time $t_3$. At this point in time, the introduced force reaches its set value $F_U$ again, and due to the further thermal expansion which becomes smaller when the green product is heated further the existing force starts to rise again, until at the point in time $t_4$ the limit $F_L$ is reached again and a further readjustment takes place.

In the middle diagram of FIG. 5 the speed is plotted during the traverse movement of the press drive.

The same holds true for the distance S which is illustrated in the bottom diagram of FIG. 5. Until the point in time $t_2$, the locked press drive prevents a motion and the force rises due to the thermal expansion. From the point in time $t_2$, the force is readjusted. Now, the position of the boundary area between green product and ram is shifted. Again, the press drive remains at the same height for the period of time $t_3$ to $t_4$. Upon reaching the limit $F_L$ at the point in time $t_4$, readjustment occurs again, and the boundary area between green product and ram is shifted further into the direction of the thermal expansion as a consequence of a further temperature increase.

It is to be noted that in FIG. 5 motions contrary to the press drive traverse direction are represented as negative motions. Likewise, moving back the press drive in the readjustment shown is considered as negative speed.

In this connection, a further aspect which is relevant according to the invention is a different coefficient of thermal expansion between the material of the muffle 24 and the material of the green product 32 which ensures relative motion upon heating, albeit clearly in the submillimeter range.

Although the present invention has been described in connection with preferred embodiments thereof, it will be appreciated by those skilled in the art that additions, deletions, modifications, and substitutions not specifically described may be made without departing from the spirit and scope of the invention as defined in the appended claims.

The invention claimed is:

1. A dental press furnace, comprising
a pressing punch (36) which acts on an ingot (32), the ingot (32) being guided in a press channel (30) which is configured in a muffle (24),
at least one of a pressure sensor, distance sensor or speed sensor detecting at least one motion parameter of the pressing punch (36), and
a control device for controlling a pressing process based on the output signal of the sensor,
wherein the control device is configured to start the pressing process based on trigger criteria, wherein the trigger criteria comprise a change of at least one motion parameter of the pressing punch upon at least one of heating and softening of the ingot which change is detected by means of the sensor,
wherein the change of at least one motion parameter of the pressing punch comprises a backward motion of the pressing punch corresponding to the thermal expansion of the ingot and wherein the trigger criterion is at least one of an end of the backward motion, a beginning of a forward motion or a defined point in time after a change of motion parameters of the pressing punch.

2. The dental press furnace as claimed in claim 1,
wherein the pressing punch acts on the ingot by means of an interposed ram (28).

3. The dental press furnace as claimed in claim 2,
wherein the control device brings the pressing punch (36) in contact with the ingot (32) before the actual pressing process by means of the interposed ram (28), and detects the thermal expansion of the ingot (32) corresponding to a motion of the pressing punch (36) against the direction of pressing, and uses the decreasing counterforce as an additional trigger criterion if no further thermal expansion takes place or upon softening.

4. The dental press furnace as claimed in claim 2,
wherein during the detection of the motion parameter the pressing punch (36) exerts a constant force or a force which follows a predefined profile onto the ingot (32) by means of the interposed ram (28) and the motion parameter is detected after the pressing punch (36) has been brought into contact with the ingot (32) by means of the ram (28).

5. The dental press furnace as claimed in claim 4,
wherein the pressing punch (36) is moved to a predefined extent which is between 0.3 and 0.5 mm.

6. The dental press furnace as claimed in claim 1,
wherein the control device causes the pressing punch (36) to exert a press force or a press power onto the ingot (32), even before the ingot (32) has softened.

7. The dental press furnace as claimed in claim 6,
wherein the control device identifies at least one of type, mass or material of the ingot (32) based on at least one of other predefined signatures or a surrounding muffle based on the muffle signature, and that the control device controls the pressing process.

8. The dental press furnace as claimed in claim 1,
wherein the firing chamber (12) of the dental press furnace (10) is set under negative pressure and the associated seals are compressed before the sensor detects the at least one motion parameter.

9. The dental press furnace as claimed in claim 1,
wherein the pressing punch (36) is moved to a predefined extent which is less than 1 mm.

10. The dental press furnace as claimed in claim 1,
wherein the ingot is made of a ceramic mass.

11. A dental press furnace, comprising
a pressing punch (36) which acts on an ingot (32), the ingot (32) being guided in a press channel (30) which is configured in a muffle (24),
at least one of a pressure sensor, distance sensor or speed sensor detecting at least one motion parameter of the pressing punch (36), and
a control device for controlling a pressing process based on the output signal of the sensor
wherein the control device is configured to start the pressing process based on trigger criteria, wherein the trigger criteria comprise a change of at least one motion parameter of the pressing punch upon at least one of heating and softening of the ingot which change is detected by means of the sensor,
wherein the trigger criterion is at least one of termination of micro impulses of the pressing punch, number of micro impulses or -temporal distance between the micro impulses.

12. A dental press furnace, comprising
a pressing punch (36) which acts on an ingot (32), the ingot (32) being guided in a press channel (30) which is configured in a muffle (24),
at least one of a pressure sensor, distance sensor or speed sensor detecting at least one motion parameter of the pressing punch (36), and
a control device for controlling a pressing process based on the output signal of the sensor
wherein the control device is configured to start the pressing process based on trigger criteria, wherein the trigger criteria comprise a change of at least one motion parameter of the pressing punch upon at least one of heating and softening of the ingot which change is detected by means of the sensor,
wherein micro impulses reflect a small and short-term motion between the end of the ingot (28) close to the pressing punch and the surrounding muffle (24).

13. A dental press furnace, comprising
a pressing punch (36) which acts on an ingot (32), the ingot (32) being guided in a press channel (30) which is configured in a muffle (24),
at least one of a pressure sensor, distance sensor or speed sensor detecting at least one motion parameter of the pressing punch (36), and
a control device for controlling a pressing process based on the output signal of the sensor,
wherein the control device is configured to start the pressing process based on trigger criteria, wherein the trigger criteria comprise a change of at least one motion parameter of the pressing punch upon at least one of heating and softening of the ingot which change is detected by means of the sensor, and
wherein below a softening temperature of the ingot (32) the sensor detects the thermal expansion of the muffle (24), which counteracts the press force of the ram (28), the pressing punch (36) and the ingot (32), the added thermal expansion thereof.

14. A dental press furnace, comprising
a pressing punch (36) which acts on an ingot (32), the ingot (32) being guided in a press channel (30) which is configured in a muffle (24),
at least one of a pressure sensor, distance sensor or speed sensor detecting at least one motion parameter of the pressing punch (36), and
a control device for controlling a pressing process based on the output signal of the sensor, wherein the control device is configured to start the pressing process based on trigger criteria, wherein the trigger criteria comprise a change of at least one motion parameter of the pressing punch upon at least one of heating and softening of the ingot which change is detected by means of the sensor, wherein the sensor senses the decreasing counterforce which corresponds to the softening of the ingot (32) due to coefficients of thermal expansion or due to differences between coefficients of thermal expansion to the control device, the control device determining the start of the pressing process to take place at a point in time after a point in time of the detection of the softening of the ingot.

15. A dental press furnace, comprising a pressing punch (36) which acts on an ingot (32), the ingot (32) being guided in a press channel (30) which is configured in a muffle (24), at least one of a pressure sensor, distance sensor or speed sensor detecting at least one motion parameter of the pressing punch (36), and a control device for controlling a pressing process based on the output signal of the sensor, wherein the control device is configured to start the pressing process based on trigger criteria, wherein the trigger criteria comprise a change of at least one motion parameter of the pressing punch upon at least one of heating and softening of the ingot which change is detected by means of the sensor, wherein based on the motion parameter detected by the sensor, at least one of press power exerted by the pressing punch (36), temperature of a temperature sensor disposed in or at the firing chamber (12), the control device identifies at least one of type, mass or material of the ingot (32) based on at least one of a heating profile or -a surrounding muffle based on a signature of the muffle, and that the control device controls the pressing process based on identified information.

16. A dental press furnace, comprising a pressing punch (36) which acts on an ingot (32), the ingot (32) being guided in a press channel (30) which is configured in a muffle (24), at least one of a pressure sensor, distance sensor or speed sensor detecting at least one motion parameter of the pressing punch (36), and a control device for controlling a pressing process based on the output signal of the sensor, wherein the control device is configured to start the pressing process based on trigger criteria, wherein the trigger criteria comprise a change of at least one motion parameter of the pressing punch upon at least one of heating and softening of the ingot which change is detected by means of the sensor, wherein the control device detects at least one of number of micro impulses (60 to 74) of the motion parameters, distances of micro impulses, change in the distances or the heights of the micro impulses.

17. A method for operating a dental press furnace (10), said dental press furnace comprising a pressing punch (36), a press channel (30), and at least one of a pressure sensor, distance sensor or speed sensor for detecting at least one motion parameter of the pressing punch (36), and a control device for controlling a pressing process based on the output signal of the at least one sensor, said method comprising:

at least one of the pressure sensor, distance sensor or speed sensor detecting a change of at least one motion parameter of the pressing punch in accordance with at least one of heating and softening of the ingot, wherein the change of at least one motion parameter of the pressing punch comprises a backward motion of the pressing punch corresponding to the thermal expansion of the ingot and wherein the trigger criterion is at least one of an end of the backward motion, a beginning of a forward motion or a defined point in time after a change of motion parameters of the pressing punch, and starting the pressing process based on the change of the at least one motion parameter.

* * * * *